(12) United States Patent
Biedermann

(10) Patent No.: US 10,667,828 B2
(45) Date of Patent: *Jun. 2, 2020

(54) INSTRUMENT GUIDE ASSEMBLY FOR A BONE PLATE AND KIT OF A BONE PLATE WITH SUCH AN INSTRUMENT GUIDE ASSEMBLY

(71) Applicant: BIEDERMANN TECHNOLOGIES GMBH & CO. KG, Donaueschingen (DE)

(72) Inventor: Markku Biedermann, Miami, FL (US)

(73) Assignee: Biedermann Technologies GmbH & Co. KG, Donaueschingen (DE)

( * ) Notice: Subject to any disclaimer, the term of this patent is extended or adjusted under 35 U.S.C. 154(b) by 591 days.

This patent is subject to a terminal disclaimer.

(21) Appl. No.: 15/412,547

(22) Filed: Jan. 23, 2017

(65) Prior Publication Data

US 2017/0209191 A1    Jul. 27, 2017

Related U.S. Application Data

(60) Provisional application No. 62/287,592, filed on Jan. 27, 2016.

(30) Foreign Application Priority Data

Apr. 29, 2016   (EP) ..................... 16167695

(51) Int. Cl.
    *A61B 17/80* (2006.01)
    *A61B 17/17* (2006.01)
    *A61B 17/00* (2006.01)

(52) U.S. Cl.
    CPC .. *A61B 17/1728* (2013.01); *A61B 2017/0042* (2013.01)

(58) Field of Classification Search
    CPC ... A61B 17/1728; B23B 47/28; B23B 47/287; Y10T 408/568
    See application file for complete search history.

(56) References Cited

U.S. PATENT DOCUMENTS 4,920,959 A * 5/1990 Witzel ................. A61B 17/645
                                                              606/53
5,507,801 A * 4/1996 Gisin .................. A61B 17/1728
                                                              606/86 R (Continued)

FOREIGN PATENT DOCUMENTS

EP         1 878 394 A2    1/2008
EP         2 168 513 A1    3/2010
WO    WO 2012/046210 A1    4/2012

*Primary Examiner* — Anu Ramana
(74) *Attorney, Agent, or Firm* — Gordon & Jacobson, P.C.

(57) ABSTRACT

An instrument guide assembly for a bone plate includes an insert configured to be arranged in a hole of a plate member, the insert having a through-hole, and a guide member separable and positionable through the through-hole of the insert, the guide member having a head portion, a shaft portion extending from the head portion, and a guide channel extending through the head and shaft portions for guiding a drill or other instrument therethrough. The insert is movable axially relative to the guide member from a first position at an end of the shaft portion opposite the head portion and past a first stop to a second position at the head portion. At the second position, the insert remains axially movable in a limited range between the first stop and the head portion, while the first stop prevents the insert from moving back to the first position.

19 Claims, 5 Drawing Sheets

(56) References Cited

U.S. PATENT DOCUMENTS

| | | | |
|---|---|---|---|
| 7,094,242 B2 * | 8/2006 | Ralph | A61B 17/1728 |
| | | | 606/96 |
| 7,648,508 B2 * | 1/2010 | Lutz | A61B 17/02 |
| | | | 606/281 |
| 2010/0082070 A1 | 4/2010 | Diez | |
| 2013/0012945 A1 * | 1/2013 | Chreene | A61B 17/1728 |
| | | | 606/80 |
| 2013/0245699 A1 | 9/2013 | Orbay et al. | |

* cited by examiner

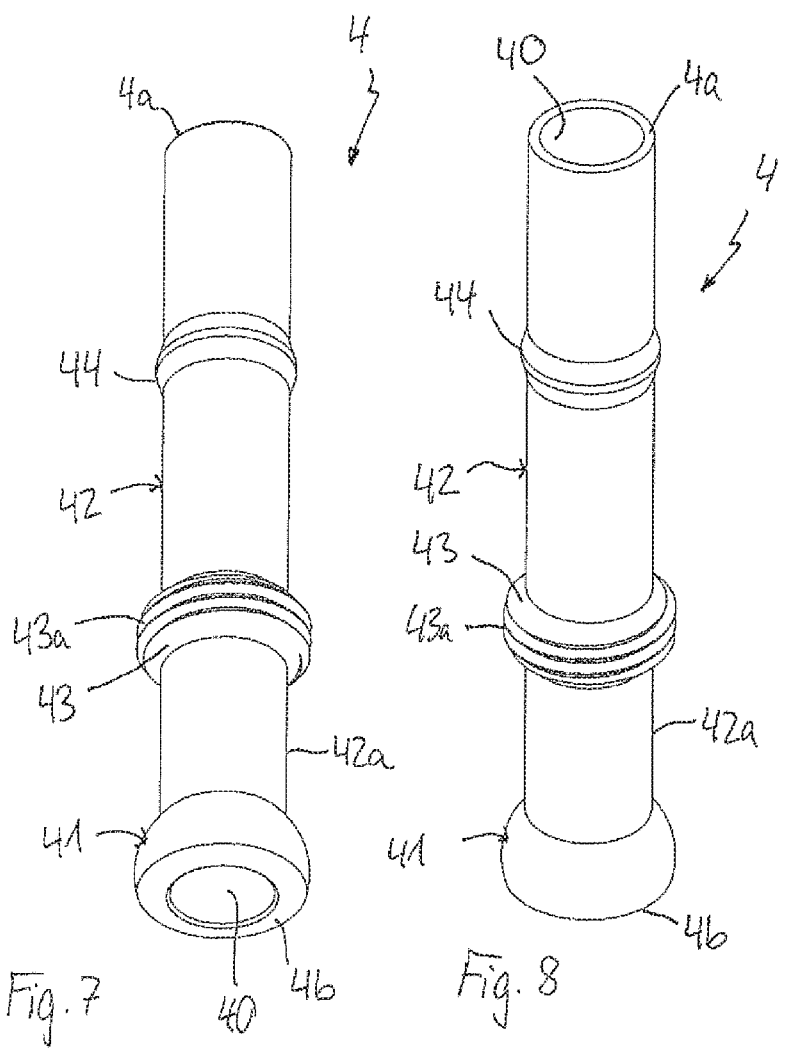
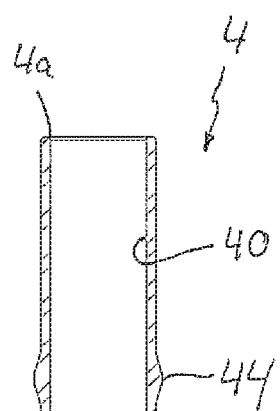
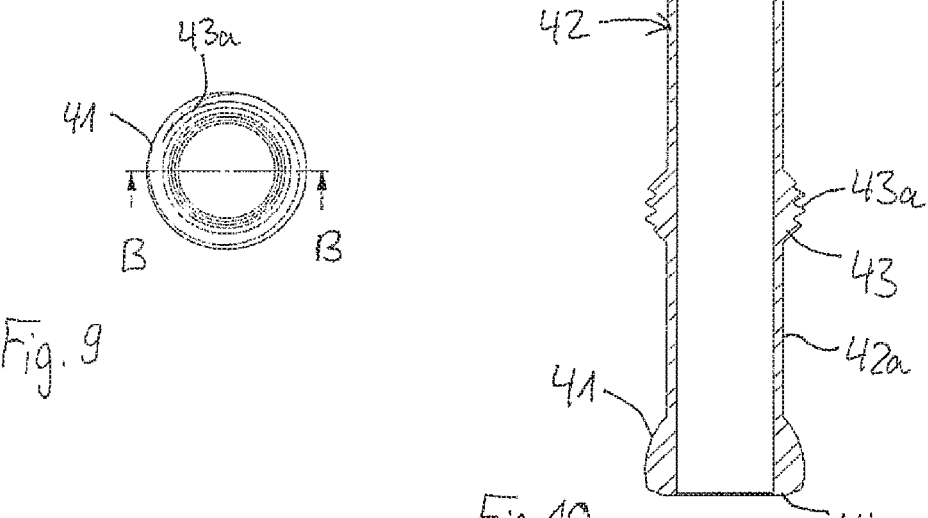

INSTRUMENT GUIDE ASSEMBLY FOR A BONE PLATE AND KIT OF A BONE PLATE WITH SUCH AN INSTRUMENT GUIDE ASSEMBLY

CROSS-REFERENCE TO RELATED APPLICATIONS

This application claims the benefit of U.S. Provisional Patent Application Ser. No. 62/287,592, filed on Jan. 27, 2016, and claims priority from European Patent Application EP 16 167 695.2, filed Apr. 29, 2016, the contents of which are hereby incorporated by reference in their entirety.

BACKGROUND

Field

The invention relates to an instrument guide assembly for a bone plate and a kit including a bone plate and such an instrument guide assembly. The instrument guide assembly includes an insert configured to be placed into a hole of a bone plate and a guide member that provides guidance for a drill bit, a guide wire, or an instrument which is used, for example, for the correct placement of the bone plate. The insert and the guide member can be connected to each other in a manner that prevents or reduces a possibility of losing the components. The instrument guide assembly is particularly useful for a bone plate that facilitates a polyaxial coupling between a bone anchor and a plate member of the bone plate.

Description of Related Art

EP 1 878 394 A2 describes an orthopaedic fixation plate system including a fixation plate including a hole with a spherically-curved inner surface and a polyaxial bushing provided in the hole. A removable guide is provided in the polyaxial bushing. The polyaxial bushing permits the surgeon to modify the angle of each guide and bushing to a selected orientation before locking the bushing at an orientation by tightening the guide into the bushing.

As generally known, for a bone plate that allows for a polyaxial coupling between a bone anchor and a plate member, it is necessary that a ball-shaped portion of the bone anchor lines up exactly with a ball-shaped seat in the plate member. Misalignment of the ball-shaped portion of the bone anchor and the ball-shaped seat in the plate member may cause stresses in the bone and may prohibit correct function of the bone plate.

WO 2012/046210 A1 describes a bone plate assembly including a plate member with at least one hole extending from a top side to a bottom side of the plate member, an insert arranged in the hole, the insert having a through-hole, and a guide member removably arranged in the through-hole of the insert, the guide member having a guide channel and an outer surface portion which engages an inner wall portion of the through-hole to allow an adjustment of an angular orientation of the guide member within the insert and relative to the plate member.

SUMMARY

Embodiments of the invention provide for an instrument guide assembly that permits easier handling and provides increased safety during use, and a kit including a bone plate and such an instrument guide assembly.

A guide member and an insert of the instrument guide assembly are coupled to each other in a manner that prevents or reduces a possibility of losing the components. When the guide member is removed from the plate member of the bone plate, the insert remains coupled to the guide member. This also increases safety during use. Also in other situations, such as for example, during sterilization, the insert remains coupled to the guide member, which also facilitates easier and safer handling of the device.

A polyaxial coupling between the insert and the guide member, and the guidance in the center of the hole of the insert for a drill allows a user to precisely define a direction of a drill bit for drilling holes in the bone. Thus, the guide member guarantees that by using a guide wire, a drill, or another tool or instrument, the trajectory of the tool or instrument is perfectly aligned with the ball-shaped seat in the plate member. This provides for a more secure and accurate bone anchor placement, to assure more proper functionality by the plate member. Further, the locking mechanism for the bone anchor and the bone is protected, even if, for example, a surgeon accidentally slips while using the drill.

After a hole for the bone anchor has been drilled into the bone using the guide member, the instrument guide assembly can be easily removed, and the bone anchor can be inserted into the hole and, in certain applications, can further be locked with a locking member.

A kit can include a plate member of a bone plate and an instrument guide assembly according to embodiments of the invention.

The kit may be provided as a modular system with various kinds of guide members, such as a guide member for a drill bit, a guide member for a K-wire, or a guide member which permits other instruments to be introduced, such as syringes for bone cement, etc. The bone plate may further include a bone anchor that can be held polyaxially in a seat of the plate member.

BRIEF DESCRIPTION OF THE DRAWINGS

Further features and advantages of the invention will become apparent from the description of embodiments, with reference to the accompanying drawings. In the drawings:

FIG. 7 shows a perspective view from a bottom of the guide member of the instrument guide assembly of FIGS. 1 and 2.

FIG. 8 shows a perspective view from a top of the guide member of FIG. 7.

FIG. 9 shows a top view of the guide member of FIGS. 7 and 8.

FIG. 10 shows a cross-sectional view of the guide member of FIGS. 7 to 9, the cross-section taken along line B-B in FIG. 9.

DETAILED DESCRIPTION

Figure 1:
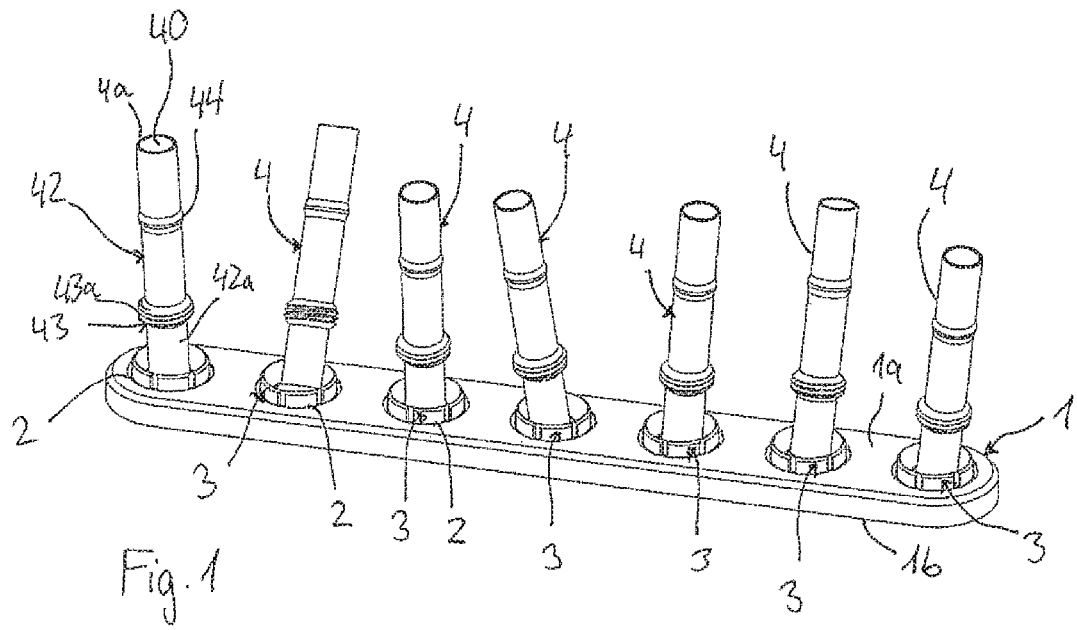
FIG. 1 shows a perspective view of a bone plate with instrument guide assemblies according to a first embodiment, where the instrument guide assemblies are placed into holes of a plate member of the bone plate.
Figure 2:
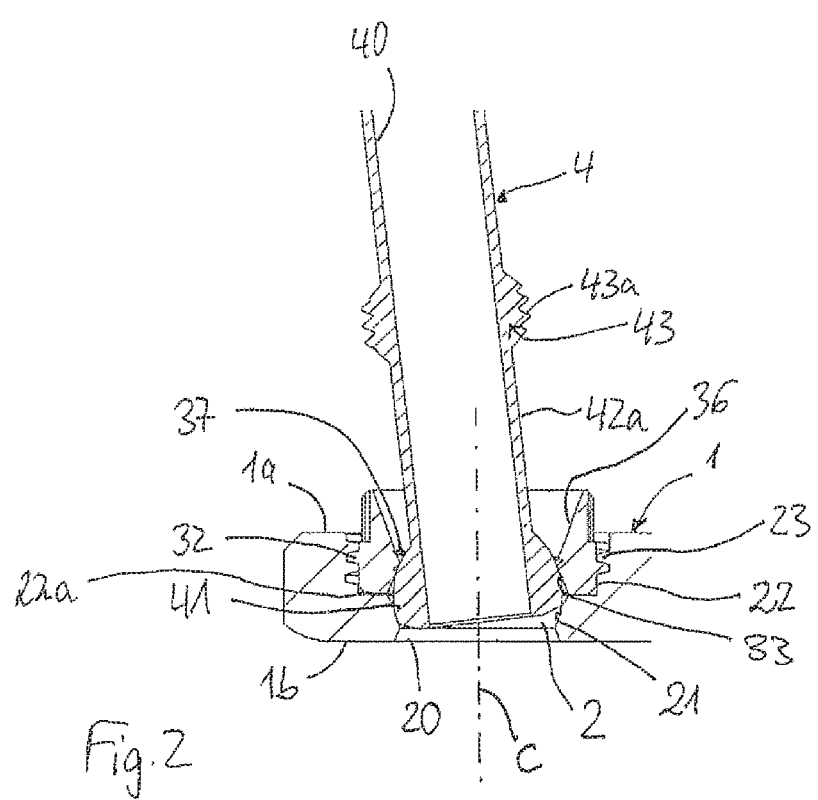
FIG. 2 shows a cross-sectional view of a portion of the plate member of FIG. 1, with an insert and a guide member forming an instrument guide assembly that is inserted at a hole of the plate member, wherein the cross-section is taken in a plane including a longitudinal axis of the hole.
Figure 3:
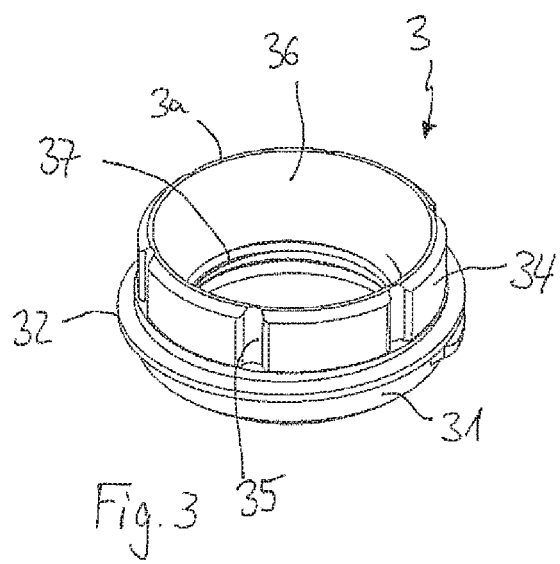
FIG. 3 shows a perspective view from a top of the insert of the instrument guide assembly of FIGS. 1 and 2.
Figure 4:
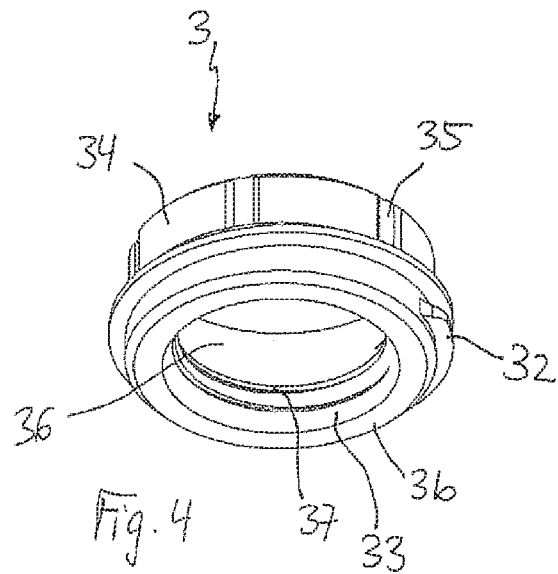
FIG. 4 shows a perspective view from a bottom of the insert of FIG. 3.
Figure 5:
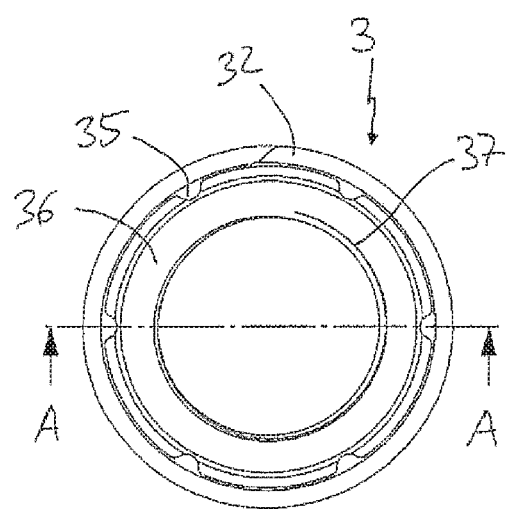
FIG. 5 shows a top view of the insert of FIGS. 3 and 4.
Figure 6:
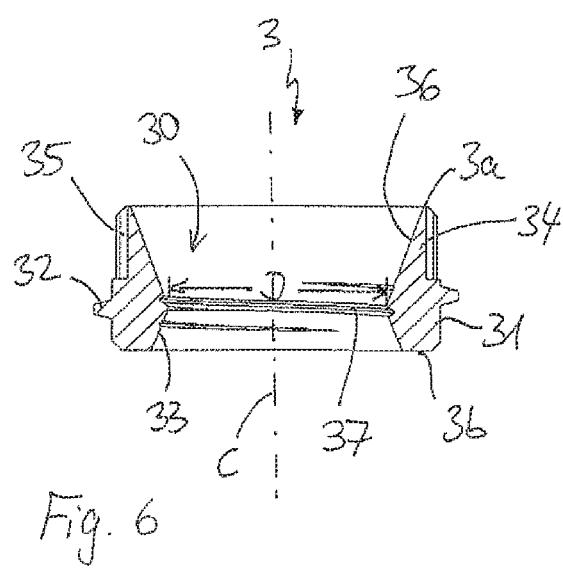
FIG. 6 shows a cross-sectional view of the insert of FIGS. 3 to 5, the cross-section taken along line A-A in FIG. 5.

A first embodiment of an instrument guide assembly and a kit including a bone plate and such an instrument guide assembly will now be described with reference to FIGS. 1 to 11d. As shown in FIGS. 1 and 2, the bone plate includes a plate member 1, which is in this embodiment a substantially elongate body with a top side 1a and a bottom side 1b. At least two, and preferably more than two, holes 2 extend through the plate member 1 from the top side 1a to the bottom side 1b. The number and arrangement of the holes 2 can vary according to the size and the shape of the plate member 1. The holes 2 are configured for receiving bone anchors (not shown), for example bone screws, to fix the plate member 1 to a bone surface, for example, to broken bone parts or to vertebrae.

In each of the holes 2, an insert 3 may be provided or attached. The inserts 3 can be removably connected to inner walls of the plate member 1 surrounding and defining each of the holes 2. A respective guide member 4 is received in each of the inserts 3. A number of inserts 3 with guide members 4 which are provided in or attached to the plate member 1 at the holes 2, can vary depending on the actual requirements or configuration of the bone plate.

As shown in particular in FIG. 2, the hole 2 has a central axis C that intersects the top side 1a and the bottom side 1b, an opening 20 towards the bottom side 1b, and a seat portion 21 adjacent to the opening 20 to receive a head of a bone anchor in a manner such that various angular orientations of an anchor axis of the bone anchor relative to the plate member 1 can be selected when the bone anchor is received in the seat portion 21. Between the seat portion 21 and the top side 1a, a cylindrical bore 22 with an internally threaded portion 23 is provided. An inner diameter of the bore 22 is larger than an inner diameter of the seat portion 21. The threaded portion 23 can have any thread form, for example, a metric thread. The threaded portion 23 can be a two-start thread or a multiple-start thread, to allow the plate member 1 to be designed with a lower profile or a smaller thickness. A bottom 22a of the bore 22 forms an abutment for the insert 3. The seat portion 21 is depicted in FIG. 2 as a seat with a spherical inner surface portion. However, the seat portion in other embodiments can have any other shape that permits insertion of a bone anchor into the bone at various angles between the anchor axis and the plate member. The seat portion 21 is arranged completely within the plate member 1, between the top side 1a and the bottom side 1b.

As shown in particular in FIGS. 2 to 6, the insert 3 is a sleeve-like piece with a top side 3a and a bottom side 3b. A through-hole 30 extends through the insert 3 from the top side 3a to the bottom side 3b. A central axis of the through-hole 30 coincides with the central axis C of the hole 2 when the insert 3 is placed in the hole 2. Adjacent to the bottom side 3b, the insert 3 includes a first portion 31 with a cylindrical outer surface and an external thread 32 that is configured to cooperate with the internal thread of the threaded portion 23 of the cylindrical bore 22. As depicted in FIG. 2, an axial length of the first portion 31 is such that the cylindrical outer surface portion of the first portion 31 can be fully inserted into the cylindrical bore 22. The through-hole 30 further has a first conically widening portion 33 that widens towards the bottom side 3b. An inner diameter of the conically widening surface 33 is such that the insert 3 can be placed onto the guide member 4 and can rest on a portion of the guide member 4, as explained in greater detail below. Between the top side 3a and the first portion 31, a second portion 34 with a cylindrical outer surface is provided, where the second portion 34 has a slightly smaller outer diameter than the first portion 31 and a length such that the second portion 34 protrudes out of the top side 1a of the plate member 1 when the insert 3 is in an inserted state in the cylindrical bore 22. A plurality of longitudinal grooves 35 that are spaced apart from each other in a circumferential direction and that extend parallel to the central axis C is provided in the outer surface of the second portion 34. The grooves 35 form an engagement structure, for example, for engaging the insert 3 with a tool to screw the insert 3 into the cylindrical bore 22 of the plate member 1, or to unscrew and remove the insert 3 from the hole 2. When the longitudinal grooves 35 are engaged by the tool (not shown), the tool can extend into a gap formed between the second portion 34 and the inner wall of the cylindrical bore 22 of the plate member 1.

The through-hole 30 further has a second conically widening portion 36 that widens towards the top side 3a. The cone angle is selected so as to permit the guide member 4 to be pivoted in a predetermined angular range when the guide member 4 is connected to the insert 3. The through-hole 30 has a smallest inner diameter D at an axial position where the first conically widening inner surface 33 and the second conically widening inner surface 36 meet. In an axial region around the smallest inner diameter D of the through-hole 30, an engagement structure in the form of an internal thread 37 is provided that is configured to engage a portion of the guide member 4. The internal thread 37 may include at least one thread turn, and preferably only a small number of thread turns, such as two or three thread turns. This facilitates a quick mounting of the insert 3 onto the guide member 4. The internal thread 37 may be a metric thread, but can also be any other thread form.

As shown in particular in FIGS. 2 and 7 to 10, the guide member 4 is formed as a substantially rotationally symmetric piece, with a top end 4a, an opposite bottom end 4b, and a guide channel 40 extending from the top end 4a to the bottom end 4b. The guide channel 40 has an inner diameter that is configured to allow a drill bit (not shown) or other instrument to pass therethrough. Adjacent to the bottom end 4b, the guide member 4 includes a head portion 41 with a spherically-shaped outer surface that is oriented such that the diameter increases towards the bottom end 4b. The guide member 4 further has a shaft portion 42 which is configured to extend out of the plate member 1 when the guide member 4 is inserted into the hole 2. The guide member 4 can serve for gripping, to adjust the position of the guide member 4 when the guide member 4 is connected to the plate member 1. The shaft portion 42 has a substantially cylindrical outer surface, but can also have other designs, such as a conical outer surface or a cylindrical outer surface, and can have different sections with different diameters.

At a distance from the head portion 41, a circumferentially extending thickened portion 43 is provided that includes an engagement structure, in the form of an external thread 43a, configured to cooperate with the internal thread 37 of the insert 3. Other parts of the shaft portion 42 are thread-free. An axial length of the thickened portion 43 may be greater than an axial length of the portion of the insert 3 with the internal thread 37. In other words, a number of thread turns at the thickened portion 43 may be greater than the number of thread turns at the internal thread 37 of the insert 3. A length of the shaft portion 42a between the head portion 41 and the thickened portion 43 is greater than an axial length of the insert 3. This allows the insert 3 to slide in an axial direction on the shaft portion 42a between the head portion 41 and the thickened portion 43. Moreover, the thickened portion 43 may have a rounded or bulge-shaped contour in an axial direction. This permits mounting of the insert 3 onto the guide member 4 without jamming.

Between the thickened portion 43 and the top end 4a, a further portion 44 may be formed that extends circumferentially around the shaft 42. The portion 44 may serve for connecting an instrument to the guide member 4, for example, an extension device. Alternatively the portion 44 may simply serve for gripping the guide member 4. An outer diameter of the thickened portion 44 is smaller than the smallest inner diameter D of the insert 3, so that the thickened portion 44 can pass through the through-hole 30 of the insert 3.

The plate member 1, the insert 3, and the guide member 4, as well as a bone anchor to be used with the plate member 1, may each be made of one or more bio-compatible materials, for example, of titanium or stainless steel, of a bio-compatible alloy, such as a NiTi-alloy, for example Nitinol, of magnesium or magnesium alloys, or from a bio-compatible plastic material, such as, for example, polyether ether ketone (PEEK) or poly-l-lactide acid (PLLA). The parts can be made of the same material or of different materials.

Figure 11A:
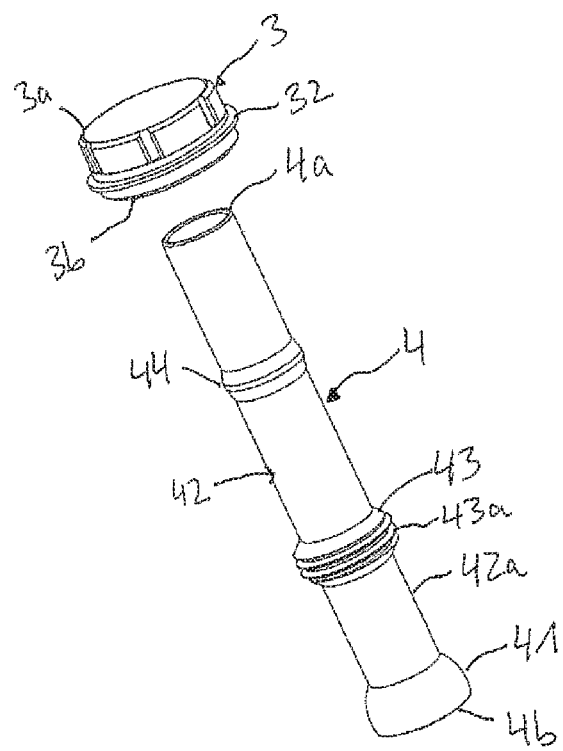
FIGS. 11a to 11d show steps of assembly of the instrument guide assembly of FIGS. 1 and 2.
Figure 11B:
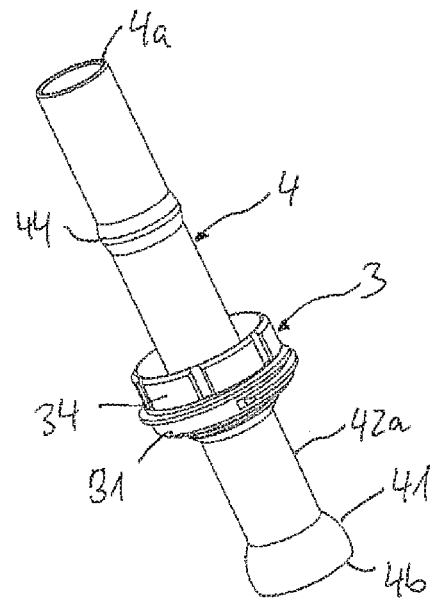
Figure 11C:
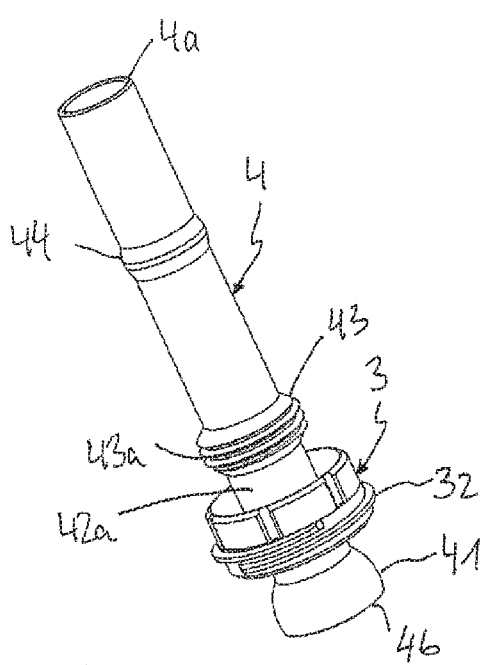

Referring now to FIGS. 11a to 11d, steps of assembling an embodiment of the instrument guide assembly will be explained. The insert 3 is placed onto the shaft 42 of the guide member 4 from the top end 4a, with the bottom side 3b facing towards the head portion 41 of the guide member 4, as depicted in FIG. 11a. The shaft portion 42 of the guide member is passed through the through-hole 30 of the insert until the internal thread 37 of the insert 3 engages the external thread 43a of the thickened portion 43 of the guide member 4, as illustrated in FIG. 11b. The insert 3 is screwed over the thickened portion 43 until the insert 3 is advanced to and positioned around the shaft portion 42a of the guide member 4, between the thickened portion 43 and the head portion 41, as shown in FIG. 11c.

Figure 11D:
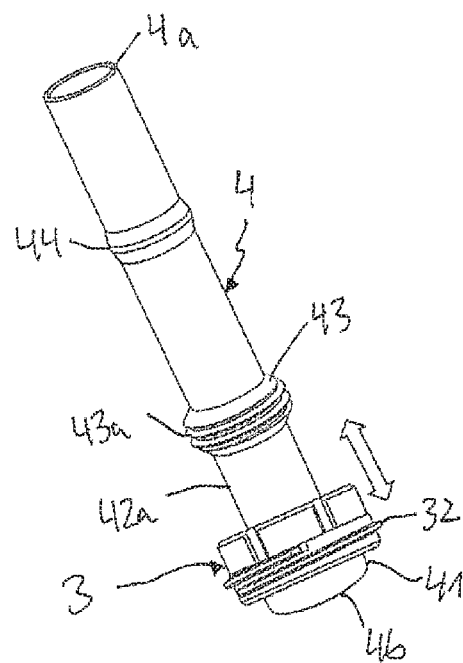
Figure 12:
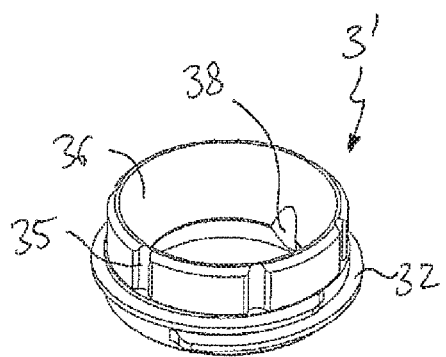
FIG. 12 shows a perspective view from a top of an insert of an instrument guide assembly according to a second embodiment.
Figure 13:
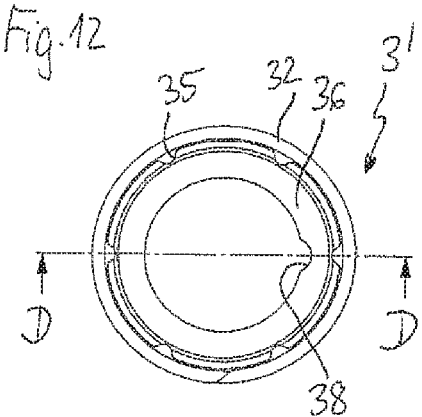
FIG. 13 shows a top view of the insert of FIG. 12.
Figure 14:
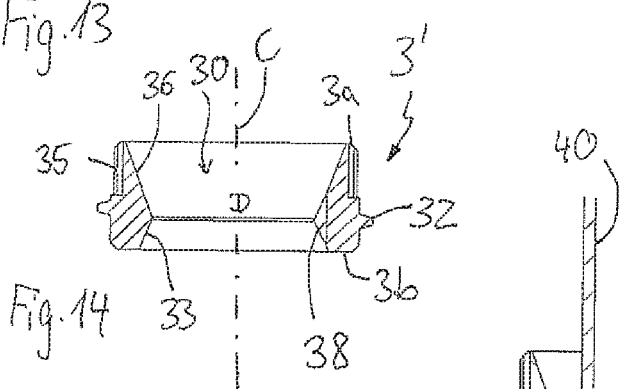
FIG. 14 shows a cross-sectional view of the insert of FIGS. 12 and 13, the cross-section taken along line D-D in FIG. 13.
Figure 15:
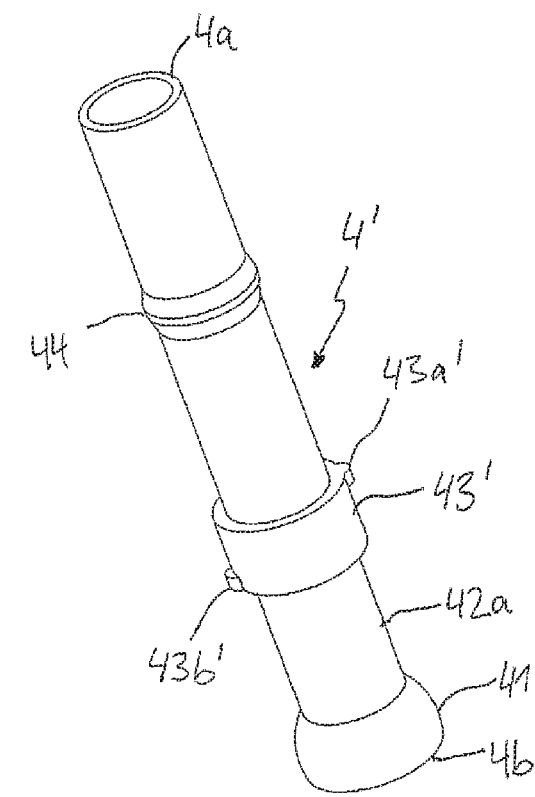
FIG. 15 shows a perspective view from a top of a guide member of the instrument guide assembly according to the second embodiment.
Figure 16:
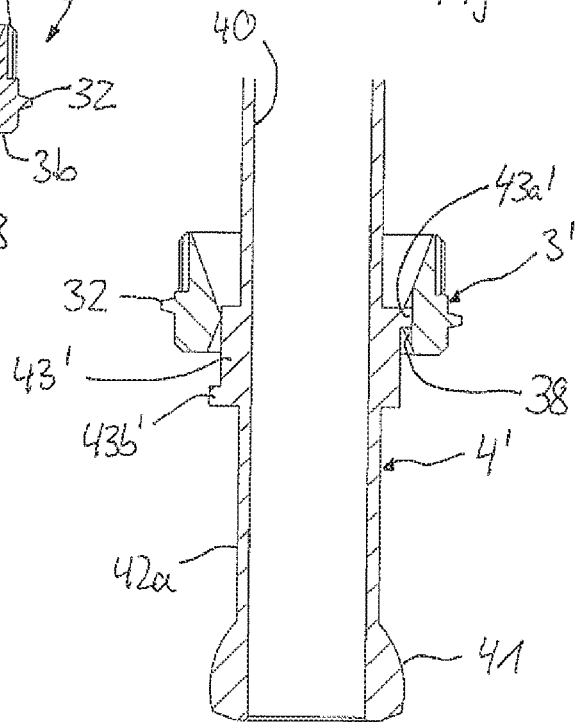
FIG. 16 shows a cross-sectional view of a step of assembling the guide member and the insert according to the second embodiment.

Then, FIG. 11d shows an assembled state between the insert 3 and the guide member 4, where the double arrow indicates that the insert 3 is movable, in particular slidable, in an axial direction between the thickened portion 43 and the head portion 41 of the guide member 4. Moreover, in this configuration, the insert 3 cannot be removed inadvertently from the guide member 4 in a direction of the top end 4a, as the thickened portion 43 acts as a first stop. Separation of the insert 3 from the guide member 4 is only possible by actively unscrewing the insert 3 from the shaft 42. Hence, the insert 3 is held on the shaft 42 in a manner such that the insert 3 cannot slide off the shaft in the direction of the top end 4a of the guide member 4, thereby preventing loss or separation of the respective parts. The insert 3 also cannot slide off from the shaft 42 of the guide member 4 in the direction of the bottom end 4b, since the head portion 41 acts as a second stop that prevents removal of the insert 3 in the direction of a second end or bottom end 4b of the guide member 4. Therefore, the insert 3 is held on the shaft portion 42 in a manner where axial movement is restricted and falling off is prevented in both directions, and where the insert 3 may still move in a limited capacity between the first stop and the second stop. In this configuration, the instrument guide assembly can be easily subjected to further steps or procedures, such as a sterilization, or can be stored, without the parts becoming separated or either the insert 3 or the guide member 4 becoming lost.

As the outer diameter of the shaft 42 is smaller than the smallest inner diameter D of the through-hole 30 of the insert 3, the guide member 4 can also be pivoted relative to the insert 3.

A use of the instrument guide assembly is as follows. When the instrument guide assembly is assembled as shown in FIG. 11d, the insert 3 is engaged with a tool that cooperates with the longitudinal grooves 35 of the insert 3, and is screwed into the cylindrical bore 22 of the plate member 1, while the guide member 4 may also be held by the tool (not shown). As shown in FIG. 2, the insert 3 can then be screwed into the cylindrical bore 22 until its bottom end 3b abuts against the bottom 22a of the cylindrical bore 22. Here, the head portion 41 of the guide member 4 is arranged in the seat 21 of the hole 2 of the plate member 1. In this position, the guide member 4 is freely pivotable relative to the plate member 1 and the insert 3. A drill bit (not shown) may be guided through the guide channel 40 of the guide member 4, and the guide member 4 can be adjusted to assume a correct or desired angular position with respect to the plate member 1, for example, an angular position that corresponds to a desired angular position of the bone anchor that is to be used for fixing the plate member 1 to the bone. Once the correct or desired angular position of the guide member 4 has been found, the hole is drilled by the drill bit. The instrument used for this assembly procedure may be configured for inserting the insert 3 into the plate member 1, and also for passing the guide member 4 and the drill bit therethrough.

After the hole has been drilled, the drill bit is removed and the insert 3 is screwed out. During this procedure, the insert 3 and the guide member 4 cannot be separated, so that neither the insert 3 nor the guide member can separately get lost in the body of the patient.

Finally, a shank of a bone anchor is passed through the hole 2 and screwed into the bone (e.g., through the previously drilled hole) until the head of the bone anchor rests in the seat 21 of the hole 2 of the plate member 1. It shall be understood that, in some embodiments, the guide member 4 can also be used for guiding through of a K-wire or another instrument to the implantation site.

In an alternative manner of use, the insert 3 may exert a certain amount of pressure onto the head portion 41 of the guide member 4, for example, by contacting the head portion 41 of the guide member 4 with the surface of the widening portion 33 when the insert 3 is tightened in the cylindrical bore 22 of the plate member 1, so that friction is generated between the head portion 41 and the insert 3. In these embodiments, an angle of the guide member 4 relative to the plate member 1 can be held at a temporary position by the friction force, and can be adjusted by applying a force that is greater than the friction force to the guide member 4. In a further alternative manner of use, the insert 3 may be sized such that the insert 3 can lock the guide member 4 at a desired angular position relative to the plate member 1 when the insert 3 is tightened in the cylindrical bore 22 of the plate member 1.

A second embodiment of the instrument guide assembly will now be explained with reference to FIGS. 12 to 16. Parts or portions which are identical or similar to that of the first embodiment are designated with the same reference numerals, and the descriptions thereof will not be repeated. In the wall defining the through-hole 30 of insert 3', an engagement structure in the form of a longitudinal groove or recess 38 that extends substantially parallel to the central axis C and that has a substantially cylinder segment-shaped contour is formed. The axial position of the recess 38 is around the region of the smallest inner diameter D. The recess 38 serves for guiding or passing through of a corresponding projection at the guide member 4'. The guide member 4' includes a thickened portion 43' in the form of a cylindrical or ring-shaped projection, with an engagement structure in the form of two distinct protrusions 43a', 43b' that protrude outward from other parts of the thickened portion 43' and that are configured to engage the recess 38 of the insert 3'. The protrusions 43a', 43b' are offset from each other by 180° in a circumferential direction, and are also offset from each other in an axial direction. The first protrusions 43a' is positioned closer to the top end 4a of the guide member 4' than the second protrusion 43b'. A distance between the protrusions 43a', 43b' in an axial direction is greater than an axial length of the recess 38 of the insert 3'. In the embodiment shown, the protrusions 43a', 43b' are respectively positioned adjacent to the upper and lower edges of the thickened portion 43'. However, the protrusions 43a', 43b' may be also located away from the upper and lower edges of the thickened portion 43' in other embodiments.

The instrument guide assembly according to the second embodiment is assembled as follows. The insert 3' is placed over the shaft 42 of the guide member 4' from the top end 4a, and is advanced over the guide member 4' in an orientation or rotational position such that the first or upper protrusion 43a' can engage the recess 38 of the insert 3'. Once the first protrusion 43a' has been guided through the recess 38 and enters the second widening portion 36 of the through-hole 30, the insert 3' can be rotated relative to the guide member 4', to a rotational orientation where the second protrusion 43b' can be guided through the recess 38. Once mounted in this manner, the insert 3' is held on the shaft portion 42 in a manner in which separation of the respective parts is prevented. When the insert 3' has to be removed, the insert 3' has to be rotated such that the lower protrusion 43b' is first guided through the recess 38, and then after rotating the guide member 4' by 180°, the upper protrusion 43a' can then be guided through the recess 38. Due to this required sequence of steps, inadvertent removal or loss of the insert 3' from around the guide member 4' is not possible after assembly.

The use of the bone plate assembly with the instrument guide assembly is the same as or similar to that discussed with respect to the first embodiment.

Modifications of the described embodiments in other ways are also conceivable. For example, any structure on the guide member that cooperates with a corresponding structure on the insert and allows an axial displacement of the insert relative to the guide member in one direction but not automatically in an opposite direction can be used. It is also conceivable, for example, to provide a spring portion with two different spring forces on the guide member that allows easy mounting of the insert in one direction by acting against a first spring force, but then prevents an inadvertent disconnection of the insert from the guide member in the opposite direction due to a second spring force that is greater than the first spring force.

The inner surface portions of the insert may also have other shapes. For example, the first conically widening inner surface portion may be replaced by a spherically-shaped surface portion, or a similar variation can be applied to the second conically widening portion. The insert may have, instead of or in addition to the drive grooves at the outer surface, other engagement portions for a tool. For example, internal drive grooves or another drive structure may be provided at an internal surface of the insert, and more specifically, the second conically widening portion may be replaced by a cylindrical surface, and the drive portion may be provided at the cylindrical inner surface. Other combinations of the shape of the drive structure and the shape of the surface of the insert that defines the drive structure may also be conceivable.

The shaft can also have various lengths, depending on the application. In particular, the shaft can have a length such that the shaft does not project out of the insert when the guide member and the insert are assembled. Moreover, the shaft can have a length such that the shaft does not project out of the plate member when the instrument guide assembly is mounted to the plate member. The guide member can be a monolithic piece or a multi part piece. For example, the shaft portion can be a separate part that can be connected to the head portion.

A kit can include a plate member of a bone plate and an instrument guide assembly according to embodiments of the invention. A modular system may include various guide members that can be assembled with an insert, to form the instrument guide assembly. The kit may also include one or more bone anchors.

In a further variation, the second stop of the instrument guide assembly may be omitted. A kit including a bone plate and such an instrument guide assembly may include a plate member with a top side, a bottom side, at least one hole extending from the top side to the bottom side, and a seat in the hole for supporting a head of a bone anchor, and the instrument guide assembly which includes an insert configured to be arranged in the hole, the insert having a through-hole, and a guide member removably arranged in the through-hole of the insert, the guide member having a head portion and a shaft portion extending from the head portion and having a longitudinal axis and a guide channel extending through the head portion and the shaft portion for guiding a drill, a K-wire, or another instrument therethrough. The head portion of the guide member is configured to be supported by the seat portion, and an inner surface portion of the insert that faces the head portion of the guide member can be conical.

The plate member can have any shape that is suitable for a bone plate.

While the present invention has been described in connection with certain exemplary embodiments, it is to be understood that the invention is not limited to the disclosed embodiments, but is instead intended to cover various modifications and equivalent arrangements included within the spirit and scope of the appended claims, and equivalents thereof.

What is claimed is:

1. An instrument guide assembly for a bone plate, comprising;

an insert configured to be arranged in a hole of a plate member of the bone plate, the insert having a through-hole; and a guide member separable from the insert and positionable through the through-hole of the insert, the guide member having a head portion comprising a spherical outer surface portion, a shaft portion extending from the head portion, and a guide channel extending through the head portion and the shaft portion for guiding a drill or other instrument therethrough, wherein the insert is movable axially relative to the guide member from a first position at on an end of the shaft portion opposite the head portion, over the shaft portion and past a first stop on the shaft portion, and to a second position at the head portion, wherein at the second position, the insert remains axially movable in a limited range between the first stop and the head portion, while the first stop prevents the insert from moving back to the first position.

2. The instrument guide assembly of claim 1, wherein the head portion forms a second stop on the guide member for limiting the insert from axially moving past the head portion.

3. The instrument guide assembly of claim 1, wherein an outer diameter of the head portion increases in a direction away from the shaft.

4. The instrument guide assembly of claim 1, wherein when the insert is at the second position, the shaft extends though the through-hole of the insert.

5. The instrument guide assembly of claim 1, wherein the guide member comprises a first engagement portion and the insert comprises a second engagement portion configured to engage the first engagement portion and wherein the first and the second engagement portions engage and disengage when the insert is moved past the first stop from the first position to the second position, and wherein the first engagement position forms the first stop when the insert is at the second position.

6. The instrument guide assembly of claim 5, wherein the first engagement portion is positioned on the shaft portion at a distance from the head portion that is greater than an axial length of the insert.

7. The instrument guide assembly of claim 5, wherein the first engagement portion and the second engagement portion comprise threaded portions.

8. The instrument guide assembly of claim 5, wherein the first engagement portion and the second engagement portion are configured to engage each other in a form-fit manner.

9. The instrument guide assembly of claim 1, wherein the insert has a top side and a bottom side, and wherein the through-hole of the insert has a smallest inner diameter at a position between the top side and the bottom side.

10. The instrument guide assembly of claim 9, wherein the through-hole has a widening section that widens from the smallest inner diameter towards the top side.

11. The instrument guide assembly of claim 9, wherein the through-hole has a widening section that widens from the smallest inner diameter towards the bottom side.

12. The instrument guide assembly of claim 11, wherein the widening section widens in a conical shape.

13. The instrument guide assembly of claim 1, wherein the insert comprises an outer surface and an engagement structure on the outer surface for engaging the plate member of the bone plate.

14. The instrument guide assembly of claim 1, wherein the insert comprises an engagement structure for engagement with a tool for inserting the insert into the hole of the plate member of the bone plate and/or for removing the insert from the hole of the plate member of the bone plate.

15. A kit comprising;
the instrument guide assembly of claim 1; and
a plate member of a bone plate, the plate member having a top side, a bottom side, at least one hole extending from the top side to the bottom side, and a seat in the hole for supporting a head of a bone anchor; wherein the head portion of the guide member is configured to be supported by the seat when the instrument guide assembly is connected to the plate member.

16. The kit of claim 15, wherein the insert comprises an outer surface and an external thread on the outer surface, and wherein the hole in the plate member of the bone plate has an internal thread configured to cooperate with the external thread of the insert.

17. A method for connecting a bone plate to a bone using an instrument guide assembly, the instrument guide assembly comprising an insert having a through-hole, a guide member separable from the insert and positionable through the through-hole of the insert, the guide member having a head portion, a shaft portion extending from the head portion, and a guide channel extending through the head portion and the shaft portion for guiding a drill or other instrument therethrough, the method comprising:

connecting the insert and the guide member by moving the insert axially on and over the shaft portion of the guide member from a first position at an end of the shaft position opposite the head portion, past a first stop, and to a second position at the head portion, wherein at the second position, the insert remains axially movable in a limited range between the first stop and the head portion, while the first stop prevents the insert from moving back to the first position;

inserting the insert into a hole of a plate member of the bone plate to connect the instrument guide assembly to the plate member, such that the head portion of the guide member is held between the insert and the plate member;

adjusting an angular position of the guide member relative to the plate member;

inserting a drill or other instrument through the guide channel of the guide member and drilling a hole in the bone with the drill or other instrument, wherein an orientation of the hole in the bone corresponds to the angular position of the guide member;

detaching the instrument guide assembly from the plate member; and connecting the bone plate to the bone by inserting a bone anchor of the bone plate through the hole of the plate member and into the hole in the bone.

18. The method of claim 17, wherein when the instrument guide assembly is connected to the plate member, a friction force is generated between the head portion of the guide member and the insert, such that when the angular position of the guide member relative to the plat member is adjusted, the guide member is held temporarily at the adjusted angular position by the friction force, and is movable out of the adjusted angular position by applying a force greater than the friction force on the guide member.

19. The method of claim 17, further comprising:
moving the insert axially relative to the guide member from the second position to the first stop;
rotating the insert to move the insert past the first stop in a direction towards the end of the shaft portion opposite the head portion; and moving the insert axially to the first position to separate the insert and the guide member from one another.

* * * * *